United States Patent
Boxer Wachler

(10) Patent No.: US 10,335,313 B2
(45) Date of Patent: Jul. 2, 2019

(54) METHOD FOR REMOVING COLORED SPOTS TO WHITEN THE EYE

(71) Applicant: Brian S. Boxer Wachler, Santa Monica, CA (US)

(72) Inventor: Brian S. Boxer Wachler, Santa Monica, CA (US)

(*) Notice: Subject to any disclaimer, the term of this patent is extended or adjusted under 35 U.S.C. 154(b) by 205 days.

(21) Appl. No.: 15/678,621

(22) Filed: Aug. 16, 2017

(65) Prior Publication Data
US 2019/0053944 A1   Feb. 21, 2019

(51) Int. Cl.
*A61F 9/007* (2006.01)

(52) U.S. Cl.
CPC .......... *A61F 9/007* (2013.01); *A61F 9/00745* (2013.01)

(58) Field of Classification Search
CPC .... A61F 9/007; A61F 9/00745; A61F 9/0079; A61F 9/008; A61F 2009/00861; A61F 9/00736; A61F 9/00754; A61F 9/013; A61F 9/00709; A61F 2009/00872; A61F 2009/00876; A61F 2009/00893; A61F 9/00
See application file for complete search history.

(56) References Cited

U.S. PATENT DOCUMENTS

| | | | |
|---|---|---|---|
| 2007/0191821 A1* | 8/2007 | Boxer Wachler | A61B 18/20 606/9 |
| 2015/0366709 A1* | 12/2015 | Roholt | A61F 9/00709 606/161 |
| 2016/0038760 A1* | 2/2016 | Hamrah | A61N 5/062 604/20 |
| 2017/0035608 A1* | 2/2017 | Boxer Wachler | A61F 9/008 |
| 2017/0209368 A1* | 7/2017 | Ni | A61K 9/0051 |

\* cited by examiner

*Primary Examiner* — Katrina M Stransky
(74) *Attorney, Agent, or Firm* — Samuel L. Alberstadt

(57) ABSTRACT

A new method whitens the eye by continuously wearing away colored spots on the conjunctiva, such as nevi and pigmented lesions. The method includes the steps of selecting an area of the conjunctiva to be removed, including a colored portion; selecting and activating a motorized conjunctiva remover, which includes a body and an eye attachment with a tip; and, applying the tip of the eye attachment to the selected area of the conjunctiva to continuously wear away the conjunctiva until it is cleared of the colored portion. The eye attachments can be supplied with a variety of different tips.

7 Claims, 2 Drawing Sheets

METHOD FOR REMOVING COLORED SPOTS TO WHITEN THE EYE

FIELD OF THE INVENTION

The present invention relates to a method for whitening the eye by removing the unsightly brown or yellow spots that can chronically appear on the conjunctiva.

BACKGROUND OF THE INVENTION

The conjunctiva is the membrane that lines the eyelid and loops back to cover the sclera, the layer covering the eye right up to the edge of the cornea. The sclera provides the eyeball with structural strength and protects against penetration and rupture. There is also a clear layer in front of the iris and pupil, which is referred to as the cornea. It helps protect the eye by keeping small foreign objects and infection-causing microorganisms out and by contributing to the maintenance of the tear film. The Tenon's capsule is underneath the conjunctiva and on top of the sclera. It contains fibroblasts, connective tissue, blood vessels, and collagen.

The white of the eye often becomes unattractive with age, affected with redness or brown and yellow colored spots. Causes can include lack of sleep, a foreign object, dust, dirt, sun damage, or pollution. PAM, or Primary Acquired Melanosis, typically develops in middle-aged or elderly patients. It almost always comprises flat, indistinct areas of conjunctival pigmentation that appear as brown or yellow spots. Certain medications, both systemic and topical, such as epinephrine-containing eye drops, may darken the conjunctiva and cause pigmented nevi, which can also arise from exposure to the industrial or photographic use of silver preparations. Systemic endocrine diseases and hormonal changes, such as those that accompany pregnancy, may lead to additional melanin production that in turn leads to darkening of the skin and even pigmentation on the conjunctiva. Benign conjunctival nevi are common and most often develop during the first decade of life, but can occur later in life to due ultraviolet light sun damage.

The discoloration of the whites of the eyes due to redness from excessive blood vessels can become chronic and can spawn self-consciousness and even social withdrawal. Over-the-counter remedies like Visine® may work if used on a limited basis and if the eyes are otherwise healthy. These "vasoconstrictors" temporarily shrink blood vessels in the white part of the eye. With overuse, however, eyes may exhibit "rebound redness" when the drops are stopped. Moreover, vasoconstrictors have no effect on brown or yellow spots on the conjunctiva.

Until now, the only permanent treatment for the discolored brown or yellow spots or nevi on the conjunctiva has been invasive surgery. This requires a sharp scalpel or scissors to cut and remove the affected conjunctiva, whose epithelial cells ultimately grow back in seven to ten days. More importantly, the invasive surgery includes a risk of cutting into the Tenon's capsule. Resulting damage to the Tenon's capsule can include unsightly scarring from hyperplastic fibroblasts and can induce permanent blood vessel reaction. The latter can lead to the complication of inducing red eyes, even if none existed before surgery. Cutting the Tenon's capsule thus has the counterproductive effect of making patients more self-conscious, which defeats the initial purpose of removing the brown or yellow spots. Moreover, damage to the Tenon's capsule can result in appreciable pain.

Laser surgery is not a viable treatment option for whitening the eye, because it presents too high a risk of elevated temperatures damaging the Tenon's capsule. High frequency ultrasound, which is principally an ablative procedure, is problematic for the same reason. Therefore, a need exists for a better device and method that can more safely whiten the eye than the current invasive surgical process, so that scarring of the Tenon's capsule can be avoided.

SUMMARY OF THE INVENTION

My new method of removing conjunctiva to whiten the eye substantially reduces the risks presented by invasive surgery, especially that of scarring the Tenon's capsule. The device used to perform this procedure preferably contains a battery-operated motor in the body portion and includes an eye attachment that is secured to the body. The motor oscillates the eye attachment back and forth, so that the tip on the eye attachment continuously wears down the conjunctiva layer-by-layer, until all of the pigmented conjunctival lesions are removed. The continuous wearing down of the conjunctiva can be finely controlled by the motor speed and by the use of different eye attachments with a variety of different tips. Unlike the sharp edge of a blade, the three dimensional surface of a finely manufactured uneven tip limits the depth that the device penetrates through the conjunctiva.

BRIEF DESCRIPTION OF THE DRAWINGS

Below is a detailed description that refers to the novel aspects of the invention, including equivalents known by those of skill in the art, and in that context refers to the following figures.

DETAILED DESCRIPTION OF THE INVENTION

Figure 1:
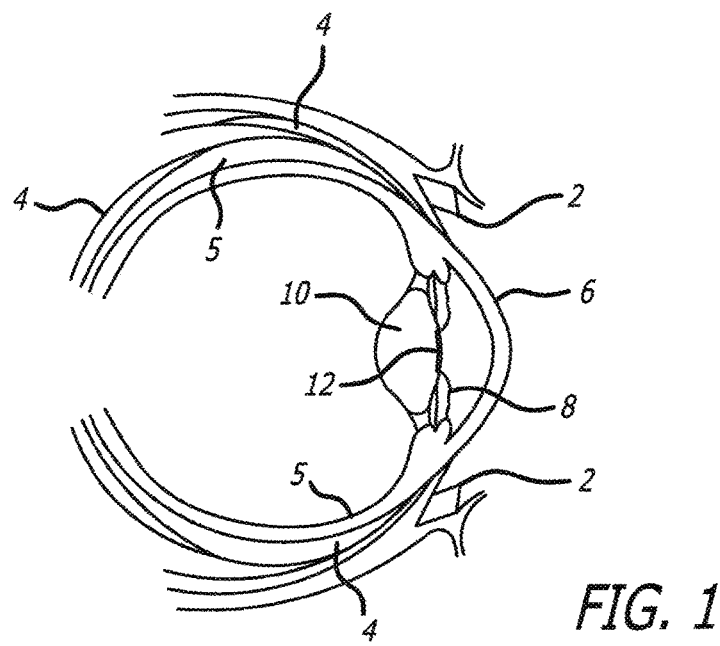
FIG. 1 depicts a cross-section view of the eye, including aspects such as the cornea, the pupil, the iris, the lens, the sclera, the conjunctiva, and the Tenon's capsule.

FIG. 1 is a cross-section of the eye in which the cornea 6, iris 8, lens 10, and pupil 12 are easily identified. The conjunctiva 2 is part of the protective covering of the inner eyelid and the eye itself. The cornea 6 covers one-sixth of the eye, while the other five-sixths is covered by the sclera 5, which is a physical continuation of the cornea and located just below the conjunctiva 2. Various aspects of the Tenon's capsule 4 are shown, and are located above the sclera 5.

Figure 2:
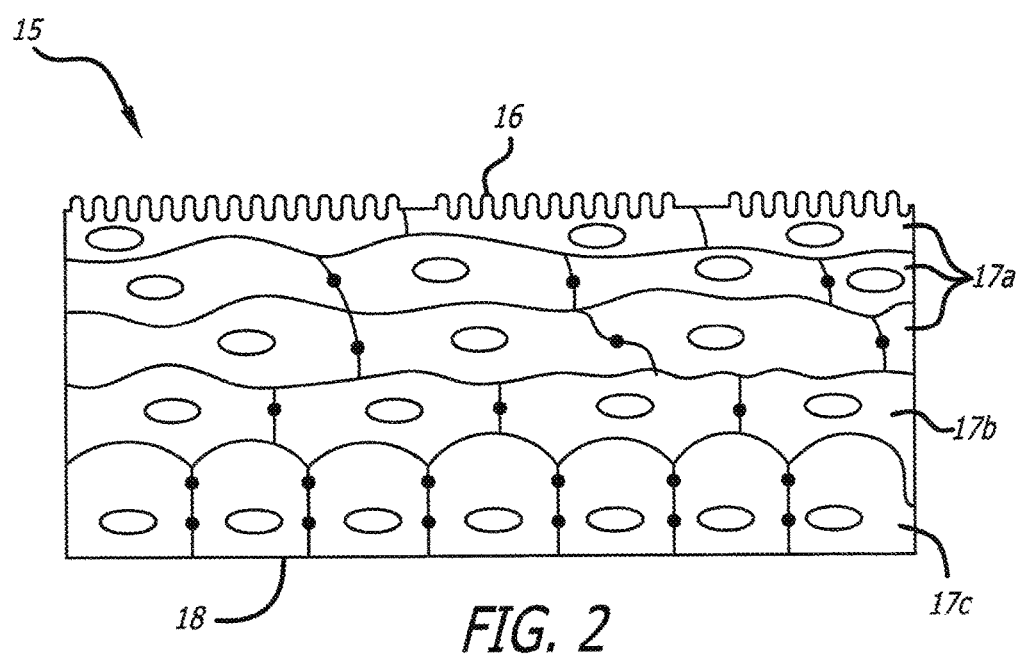
FIG. 2 is a cross-section view of the multicellular nature of the conjunctiva.

FIG. 2 is a cross-section of the conjunctiva 15 that is continuously worn away, layer by layer, by the present invention. The outer or anterior surface 16 of the conjunctiva 15 is microscopically uneven to help hold the tear film on the outside of the eye. The top three layers 17a are flattened surface cells. The basal cells form a single columnar layer of cells 17c that adjoins the basal lamina 18. Between surface cells 17a and basal cells 17c are two to three layers of elongated wing cells 17b.

Figure 3:
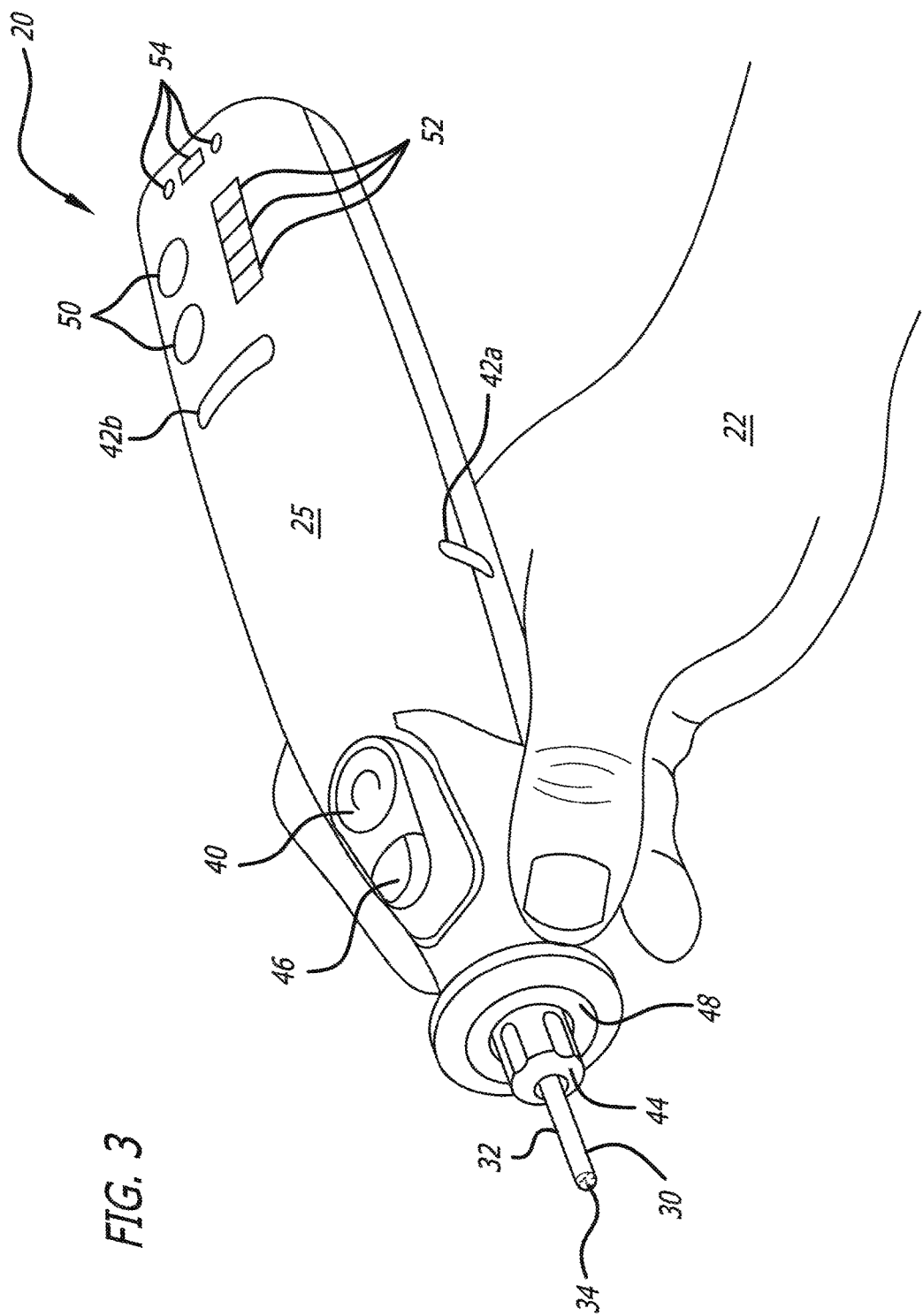
FIG. 3 is a perspective view of a device for removing colored spots from the white of the eye.

FIG. 3 depicts my invention 20 that is used to perform the method of whitening the eye that is the subject of this application. Commercially the method is one of multiple techniques for conjunctivoplasty that I refer to as I-BRITE®. Invention 20, which will also be referred to as conjunctiva remover 20, is a device for removing colored spots from the white of the eye. It generally consists of two parts, body 25 and eye attachment 30 and is held like a pencil between the thumb and forefinger of hand 22. Inside body 25 is a small electric motor (not shown) that vibrates eye attachment 30 and that is powered by rechargeable batteries (not shown). The power is controlled by on-off switch 40. Vents 42a and 42b permit air-cooling of the motor. Eye attachment 30 includes hemispherical tip 34 and shaft 32, the latter secured by locking nut 44 and shaft lock button 46. As with electric drills, a chuck (not shown) could be used to secure shaft 34 of eye attachment 30. Front light 48 provides the user with close, direct light on the eye being worked on. When invention 20 is operated, tip 34 of eye attachment 30 wears away the conjunctiva layer by layer, until the discolored spot has been removed.

Controls 50 and 52 provide a variety of options, depending upon how the conjunctiva remover 20 is designed. In one embodiment, as suggested above, body 25 contains an electric motor (not shown) that vibrates eye attachment 30. Controls 50 and 52 allow the user to control the oscillation speed of eye attachment 30. Likewise, the conjunctiva remover 20 could also include a motor and controls 50 and 52 enabling eye attachment 30 to move side-to-side in a direction perpendicular to the long axis of body 25. Given the delicate nature of eye surgery, these movements would be extremely small, on the order of micrometers. In addition, eye attachment 30 can be manufactured with a variety of tips 34. One such tip has an uneven surface that slowly wears away the conjunctiva until the Tenon's capsule is reached. Only the conjunctiva including or overlying the area above and around the colored spots need be removed, not the entire conjunctiva. This can be accomplished with a very, very fine but uneven tip surface.

The new method of removing pigmented lesions from the conjunctiva includes the following steps. Once the patient has been prepared in the procedure room, topical anesthetic gel or drops are applied after which the ocular surface is prepared using disinfectant. Then, an ocular speculum is inserted to continually expose the eye. At this point, if not before, the physician selects an eye attachment and secures it to the body of the device. Then he or she turns on the device and delicately applies the tip 34 of eye attachment 30 to the affected area of the conjunctiva. The oscillating motion of tip 34 continuously wears away the conjunctiva, layer by layer. This is not necessarily a uniform or continuous process. The physician may stop to remove some of the treated conjunctiva before continuing, and at some point he or she may decide to change eye attachments. Ultimately he or she removes all the pigmented conjunctiva and any surrounding conjunctiva that he or she deems appropriate. Then he or she powers off the oscillating tip 34 of eye attachment 30 and removes the eyelid speculum. Finally, he or she completes the procedure by topically applying antibiotic and anti-inflammatory eye drops.

In using the invention the physician has several choices. Tip 32 can have a variety of wearing surfaces from fine to coarse, as those terms are considered in relation to the delicacy of the conjunctiva. Likewise, the tip 34 of eye attachment 30 can come in different shapes to accommodate different eyes and different problems. While tip 34 of eye attachment 30 in FIG. 3 is generally hemispherical with a fine but uneven surface for wearing off the conjunctiva, other eye attachments could be oblate, flat, or even slightly concave to conform to the shape of the eye. Tip surfaces could also be made brush-like. It is anticipated, however, that most tips will have a unitary structure, regardless of whether they are cast, laser-cut, or otherwise manufactured. Using multiple tips 34 with the different eye attachments 30 that can be moved in different ways by controls 50 and 52 provide the physician with an assortment of options for removing colored spots on the eye.

Although the inventor has described what he considers the best mode of carrying out the invention, it will be apparent to those skilled in the art that modifications, variations, and equivalents can be made without departing from the scope of the invention as detailed in the claims below. For example, instead of using batteries the motor can be directly connected to an electrical outlet or to a console that could have control features instead of, or together with, the conjunctiva remover. In another variation, the motor could be battery-operated but the device could be controlled from the console. For security, the console could require a key card for activation. As noted, different motor speeds, different eye attachments and surfaces, and even different motions of the eye attachment could be used as circumstances require.

What is claimed:

1. A method for whitening an eye by removing pigmented lesions, nevi, and colored spots from the conjunctiva of the eye, comprising the steps of:
    topically applying an anesthetic to the eye;
    preparing the ocular surface with a disinfectant;
    inserting an eyelid speculum;
    selecting an area of the conjunctiva to be removed, including a colored portion;
    selecting and activating a motorized conjunctiva remover, which includes a body and an eye attachment with a tip, and which has a long axis along the length of the conjunctiva remover;
    applying the tip of the eye attachment to the selected area of the conjunctiva to continuously wear away the conjunctiva until it is cleared of the colored portion;
    deactivating the conjunctiva remover;
    removing the eyelid speculum; and,
    topically administering an antibiotic substance and an anti-inflammatory substance.

2. The method of claim 1, wherein the conjunctiva is continuously worn away layer by layer.

3. The method of claim 1, wherein the motorized conjunctiva remover oscillates the tip of the eye attachment along an axis perpendicular to the long axis of the conjunctiva remover.

4. The method of claim 2, wherein the tip of the eye attachment is generally shaped in the form of a hemisphere.

5. The method of claim 2, wherein the tip of the eye attachment is flat.

6. The method of claim 2, wherein the tip of the eye attachment is concave.

7. The method of claim 2, wherein the tip of the eye attachment is brush-like.

* * * * *